United States Patent [19]

Budde et al.

[11] 4,067,973
[45] Jan. 10, 1978

[54] 2-((2-CHLOROPHENYL)AZO)IMIDAZOLES AND THEIR USE AS AN ANTHELMINTIC

[75] Inventors: Paul B. Budde; Robert D. Vatne, both of Midland, Mich.

[73] Assignee: The Dow Chemical Company, Midland, Mich.

[21] Appl. No.: 754,729

[22] Filed: Dec. 27, 1976

[51] Int. Cl.² .............................................. A61K 31/655
[52] U.S. Cl. ...................................................... 424/226
[58] Field of Search ........................................... 424/226

[56] References Cited
PUBLICATIONS

Komatsu — Chem. Abst., vol. 74 (1971), pp. 65537c, 65540y, 113183h.

Primary Examiner—Sam Rosen
Attorney, Agent, or Firm—S. Preston Jones; C. Kenneth Bjork

[57] ABSTRACT 2-((2-Chlorophenyl)azo)imidazole and its hydrochloride salt and its dimethyl iodide derivative were prepared and employed as anthelmintics for the control of gastrointestinal nematodes (worms) in animals and more specifically for the control of Haemonchus in ruminant animals.

9 Claims, No Drawings

2-((2-CHLOROPHENYL)AZO)IMIDAZOLES AND THEIR USE AS AN ANTHELMINTIC

BACKGROUND OF THE INVENTION

Helminthiasis, the infestation of an animal by certain species of parasitic worms, is one of the most common, serious and widespread animal diseases. Of special interest are those parasitic worms of the family *Trichostrongylidae* and the genus *Haemonchus*. These parasites have the common name twisted stomach worm and cause the disease in ruminants known as haemonchosis, stomach worm disease or wireworm disease. These worms have been found to invade the abomasum of sheep, cattle, goats, moose, deer, bison and a number of other ruminants.

The above parasites during their maturation and growth have a very deleterious effect upon the animal and its rate of growth. In the intestine, the parasites erode the epithelial tissues bringing about hemorrhage, anemia, weakness and tissue necrosis. Animals if they do not succumb to gross parasitism, are rendered economically unfit by weakness, lower vitality and poor growth and reproduction. The economic loss to the cattle and sheep industry of the United States from gross parasitism is extremely high.

While many drugs have been developed to try and offset the effects of these diseases, they have not been completely satisfactory for a variety of reasons. In some cases the drugs have not been sufficiently effective, and in others, the cost of the drug has been too high and in many cases the parasites have developed a resistance to the drug.

SUMMARY OF THE INVENTION

The present invention is directed to a method of controlling gastrointestinal nematodes in animals and more specifically controlling the nematode of the genus Haemonchus in sheep.

The active anthelmintic agents are 2-((2-chlorophenyl)azo)imidazole of the formula

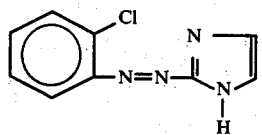

and its hydrochloride salt and 2-((2-chlorophenyl)azo)-1,3-dimethyl imidazole iodide of the formula

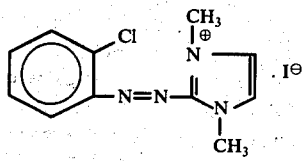

The imidazoles of the present invention are crystalline solids and can be prepared by diazotizing 2-chloroaniline at a temperature of about 0° C with a diazotizing agent followed by reacting the thus formed diazonium salt with imidazole to form the 2-((2-chlorophenyl)azo)imidazole and thereafter treating this compound with hydrogen chloride or hydrochloric acid in the presence of a solvent to form the hydrochloride salt. The 2-((2-chlorophenyl)azo)-1,3-dimethyl imidazole iodide derivative is formed by refluxing the imidazole compound for about 1-4 hours with an excess of methyl iodide in the presence of a solvent.

The practice of the present invention can be accomplished by the oral administration of an anthelmintically effective amount of the hereinabove set forth imidazole compounds. The administration of a therapeutic or prophylactic dose, or dose sufficient to control the nematodes without serious toxic effects on sheep, is essential and critical for the practice of the present invention. The exact dose to be administered may vary provided the required anthelmintic dosage is provided and is dependent upon the specific agent to be employed, as well as upon whether the administration is to be made in a single dose or in multiple doses over a period of several days. Where a single dose is employed, good results are obtained when the compounds are administered at a dosage of from about 5 to about 500 milligrams per kilogram of body weight (mg/kg) of the animal and preferably from about 25 to about 50 mg/kg of body weight.

The administration can be carried out by the feeding of the unmodified imidazole compounds. However, the present invention also embraces the employment of a liquid drench, powder, mash, pellet, bolus or other animal feed composition containing the imidazole derivatives. In such usage, the compounds may be modified with one or a plurality of additaments or innocuous ingestible adjuvants such as water, ethanol, skimmed milk, syrups, edible oils, surface active dispersing agents such as the liquid and solid dispersing or emulsifying agents; and edible solid carriers such as edible powders, mineral and vitamin supplements and commercial feeds, concentrates and supplements.

For direct oral administration to animals, both solid and liquid compositions containing from about 1 to about 95 percent by weight of the imidazole derivatives can be employed to supply the desired dosage. Where the compounds are provided as a constituent of the principal food ration, satisfactory results are obtained with food rations containing a minor but effective amount of the imidazole derivatives. The exact amount of the compound to be incorporated in the ration is dependent upon the food consumption and feeding habits of the animals concerned. For best results, it is preferred that the animal receive a dosage of from about 5 to about 500 mg/kg of body weight per day. Where the compound is provided as a constituent of feed supplements, good results are obtained with supplements containing from 0.1 to 5 percent by weight of the imidazole derivatives. In compositions to be employed as concentrates, the active agents can be present in a concentration of from 2 to 98 percent by weight.

Liquid compositions containing the desired amount of the imidazole derivatives can be prepared by dissolving the compounds in an edible solvent or oil or by dispersing them in water with the aid of a suitable surface active dispersing agent such as an ionic or non-ionic emulsifying and dispersing agent. Suitable surface active agents include the glycerol and sorbitan esters of fatty acids and the polyoxyalkylene derivatives of fatty alcohols and sorbitan esters. The aqueous compositions can contain one or more inert water-immiscible oils as a solvent for the active agent. In such compositions, the water, oil and emulsifying agent constitute an aqueous emulsion carrier.

In the preparation of solid feed compositions, the imidazole compounds can be mechanically mixed with an inert finely divided edible solid such as flour or animal feed or a solid surface active dispersing agent such as finely divided bentonite, fuller's earth or attapulgite. These compositions can be administered in the form of bolus, capsule or tablet, or dispersed in an animal feed and such feed used to supply a part or the entire food ration. Alternatively, the imidazole compounds can be dissolved in an organic solvent, the resulting mixture dispersed in an animal feed and the feed dried to remove the solvent. Also the compounds can be dispersed in an edible oil such as coconut oil, olive or peanut oil and the resulting mixture dispersed in the feed. These edible oil compositions can contain one of the aforementioned surface active agents.

The finished feed should contain protein, fat, fiber, carbohydrate, vitamins and minerals, each in an amount sufficient to meet the nutritional requirements of the animal for which the feed is intended. Most of these substances are present in naturally occurring feed materials, such as alfalfa hay or meal, cracked corn, whole oats, soybean oil meal, corn silage, ground corn cobs, wheat bran, and dried molasses. Bone meal, limestone, iodized salt and trace minerals are frequently added to supply the necessary minerals, and urea to provide additional nitrogen.

As is well known to those skilled in the art, the types of diets are extremely variable depending upon the purpose, type of feeding operation, species, etc. Specific diets for various purposes are listed by Morrison in the Appendix of "Feeds and Feeding," The Morrison Publishing Company, Clinton, Iowa, 1969.

The following examples merely illustrate the invention and a manner by which it can be practiced and are not to be construed as limiting.

EXAMPLE 1

2-((2-Chlorophenyl)azo)imidazole

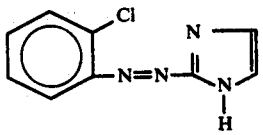

To a mixture of 750 cubic centimeters (cc) of ice water and 250 cc of concentrated hydrochloric acid which was stirred and cooled to ~0° C was added 128.0 grams (1.0 mole) of 2-chloroaniline. Immediately a white solid formed. This mixture was stirred at ~0° C as 69.0 grams (1.0 mole) of sodium nitrite was added over a period of ~15 minutes. After the completion of the addition, the newly formed solution was stirred for ~15 minutes and 68.0 grams (1.0 mole) of imidazole was added. After a short period, 5.0 liters of water was added and the temperature was brought to ~0° C. To this mixture was slowly added with vigorous stirring 160.0 grams of anhydrous sodium carbonate and the mixture thereafter stirred at ~0° C for 3.0 hours. At the end of the period, the solution was filtered and the solid which was recovered was washed with water. The solids were thereafter mixed with dilute hydrochloric acid (200 cc of concentrated hydrochloric acid diluted to 2.0 liters) and stirred at room temperature for ~1.0 hour. The insolubles were removed by filtration and discarded. The filtrate was made basic with 140.0 grams of sodium carbonate and the crystals which formed were removed by filtration, washed with water and dried to give 213.5 grams of crude 2-((2-chlorophenyl)azo)imidazole melting at 173°–177° C.

This above crude product was thereafter twice recrystallized from ethanol to yield 60.6 grams (69.2 percent of theoretical) of the purified product melting at 195°–196° C.

This above compound is taught in Khim. Geterotsikl Soedin, pages 916–922 (1969) [C.A. 72. 1114272].

EXAMPLE 2

2-((2-Chlorophenyl)azo)imidazole: hydrochloride

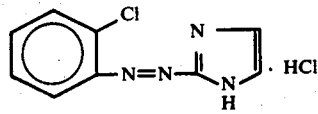

2-((2-Chlorphenyl)azo)imidazole (41.2 grams; 0.2 mole) was treated at room temperature with 40.0 cc of concentrated hydrochloric acid in 600 cc of ethanol to yield 50.0 grams (99.6 percent of theoretical) of 2-((2-chlorophenyl)azo)imidazole hydrochloride melting at 185°–186° C.

EXAMPLE 3

2-((2-Chlorophenyl)azo)-1,3-dimethyl imidazole iodide

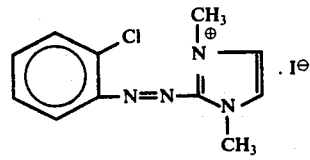

2-((2-Chlorophenyl)azo)imidazole (20.6 grams; 0.1 mole) was refluxed with 50 cc of methyl iodide in 100 milliliters of glyme for 2.0 hours to give 22.0 grams (60.8 percent of theoretical) of 2-((2-chlorophenyl)azo)-1,3-dimethylimidazole iodide melting at 212°–215° C.

EXAMPLE 4

A study was carried out to determine the anthelmintic efficacy of the hereinafter set forth compounds in the kill and control of *Haemonchus* in sheep.

Test Method:

Sheep which were of the approximate same age and which were naturally infected with the gastrointestinal nematode *Haemonchus* were selected at random to receive, by oral administration, in a single dose, a gelatin capsule containing a predetermined amount of one of the hereinafter set forth compounds.

The efficacy of the compounds was evaluated by comparing the average of two pretreatment counts of eggs per gram of feces and the average of two post-treatment counts of eggs per grams of feces. The pretreatment egg counts were made on days 1 and 2 prior to the administration of the compound and the average of the two counts was employed. The post-treatment egg counts were made on days 6 and 7 after administration of the compound and the average of the two counts was employed.

The results of this comparison, the compounds employed and the dosage administered are set forth below in Table I.

TABLE I

| Compound | Dosage rate in milligrams per kilogram of animal weight (mg/kg) | Percent reduction in egg count per gram of feces |
| --- | --- | --- |
| 2-((2-chlorophenyl)azo)imidazole | 100 | 80 |
| 2-((2-chlorophenyl)azo)imidazole hydrochloride | 72 | 78 |
| 2-((2-chlorophenyl)azo)-1,3-dimethyl imidazole iodide | 150 | 85 |
| Control | — | 0 |

EXAMPLE 5

By following the testing procedure as set forth in Example 4, the following results were also obtained for 2-((2-chlorophenyl)azo)imidazole with additional sheep. The results of these additional studies are set forth below in Table II.

TABLE II

ANTHELMINTIC EFFICACY IOF 2-(2-CHLOROPHENYL-AZO) IMIDAZOLE AGAINST *HAEMONCHUS* IN SHEEP

| ANIMAL # | RATE (MG/KG) | % E.P.G. REDUCTION* |
| --- | --- | --- |
| 1 | 300 | 90 |
| 2 | 200 | 75 |
| 3 | 200 | 74 |
| 4 | 193 | 32 |
| 5 | 127 | 96 |
| 6 | 120 | 96 |
| 7 | 100 | 62 |
| 8 | 100 | 98 |
| 9 | 92 | 82 |
| 10 | 75 | 28 |
| 11 | 51 | 82 |
| 12 | 50 | 16 |
| 13 | 50 | 0 |
| 14 | 50 | 97 |
| 15 | 50 | 90 |
| 16 | 20 | 68 |

*Eggs per gram reduction; efficacy based on two pre- and two post-treatment fecal samples.

What is claimed is:

1. A composition useful for the control of *Haemonchus* in ruminant animals which comprises an inert carrier and from 1 to 95 percent by weight of 2-((2-chlorophenyl)azo)-1,3-dimethyl imidazole iodide.

2. A method for the control of *Haemonchus* in ruminant animals which comprises orally administering to said animals, an anthelmintically effective amount of a compound selected from the group consisting of 2-((2-chlorophenyl)azo)imidazole, 2-((2-chlorophenyl)azo)imidazole:hydrochloride and 2-((2-chlorophenyl)azo)-1,3-dimethyl imidazole iodide.

3. The method of claim 2 wherein the compound is 2-((2-chlorophenyl)azo)imidazole.

4. The method of claim 2 wherein the compound is 2-((2-chlorophenyl)azo)imidazole:hydrochloride.

5. The method of claim 2 wherein the compound is 2-((2-chlorophenyl)azo)-1,3-dimethyl imidazole iodide.

6. An animal feed composition which comprises an animal feed containing from 2 to 98 percent by weight of a compound selected from the group consisting of 2-((2-chlorophenyl)azo)imidazole, 2-((2-chlorophenyl)azo)imidazole:hydrochloride and 2-((2-chlorophenyl)azo)-1,3-dimethyl imidazole iodide.

7. The composition of claim 6 wherein the compound is 2-((2-chlorophenyl)azo)imidazole.

8. The composition of claim 6 wherein the compound is 2-((2-chlorophenyl)azo)imidazole:hydrochloride.

9. The composition of claim 6 wherein the compound is 2-((2-chlorophenyl)azo)-1,3-dimethyl imidazole iodide.

* * * * *

UNITED STATES PATENT AND TRADEMARK OFFICE
CERTIFICATE OF CORRECTION

PATENT NO. : 4,067,973

DATED : January 10, 1978

INVENTOR(S) : Paul B. Budde and Robert D. Vatne

It is certified that error appears in the above-identified patent and that said Letters Patent are hereby corrected as shown below:

Column 3, line 33 "1969" should read --1959--;

Column 4, line 20 "2-((2-Chlorphenyl)azo)imidazole" should read --2-((2-Chlorophenyl)azo)imidazole--;

Column 4, line 24 "chlorophenyl)azo)imidazole hydrochloride" should read --chlorophenyl)azo)imidazole: hydrochloride--;

Column 5, line 27 TABLE II "ANTHELMINTIC EFFICACY IOF" should read --ANTHELMINTIC EFFICACY OF--;

Column 6, line 2 TABLE II-continued, "ANTHELMINTIC EFFICACY IOF" should read --ANTHELMINTIC EFFICACY OF--.

Signed and Sealed this

Tenth Day of October 1978

[SEAL]

Attest:

RUTH C. MASON
*Attesting Officer*

DONALD W. BANNER
*Commissioner of Patents and Trademarks*